United States Patent
McKegney et al.

(10) Patent No.: US 7,523,070 B2
(45) Date of Patent: *Apr. 21, 2009

(54) MANAGING A VIRTUAL PERSONA THROUGH SELECTIVE ASSOCIATION

(75) Inventors: Ross McKegney, Toronto (CA); Darshanand Khusial, Mississauga (CA); Lev Mirlas, Thornhill (CA); Victor Chan, Thornhill (CA)

(73) Assignee: International Business Machines Corporation, Armonk, NY (US)

( * ) Notice: Subject to any disclaimer, the term of this patent is extended or adjusted under 35 U.S.C. 154(b) by 52 days.

This patent is subject to a terminal disclaimer.

(21) Appl. No.: 11/751,236

(22) Filed: May 21, 2007

(65) Prior Publication Data

US 2007/0214089 A1 Sep. 13, 2007

Related U.S. Application Data

(63) Continuation of application No. 10/953,990, filed on Sep. 29, 2004, now Pat. No. 7,321,877.

(51) Int. Cl.
*G06Q 99/00* (2006.01)
(52) U.S. Cl. .................... 705/51; 707/100; 709/228; 705/1
(58) Field of Classification Search ............ 705/80, 705/10, 8, 26, 1; 709/228; 707/100
See application file for complete search history.

(56) References Cited

U.S. PATENT DOCUMENTS

| | | | |
|---|---|---|---|
| 2002/0078212 A1* | 6/2002 | Besaw et al. | 709/228 |
| 2003/0050932 A1* | 3/2003 | Pace et al. | 707/100 |
| 2004/0019494 A1* | 1/2004 | Ridgeway et al. | 705/1 |

OTHER PUBLICATIONS

Giles, Roosevelt, Electronic commerce, May 1997, Network VAR, vol. 5, No. 5.*

* cited by examiner

*Primary Examiner*—James P Trammell
*Assistant Examiner*—Behrang Badii
(74) *Attorney, Agent, or Firm*—Dillon & Yudell LLP

(57) ABSTRACT

A technique is provided to generally provide user support across multiple accounts by allowing a single person or user to represent multiple organizations. An embodiment may typically provide support for a user to act on behalf of an account in the form of a virtual persona and also to provide the ability to manage the assignment of access rights allowing only prescribed privileged users to act on behalf of an account. This may then be accomplished through registration of a single identity for the user or person on the system, while allowing that person to then select the desired organization to represent for a particular session (which will be stored in the user's session).

20 Claims, 3 Drawing Sheets

MANAGING A VIRTUAL PERSONA THROUGH SELECTIVE ASSOCIATION

RELATED APPLICATION

The present application is a continuation of U.S. patent application Ser. No. 10/953,990 filed on Sep. 29, 2004, now U.S. Pat. No. 7,321,877 and entitled "Managing a Virtual Persona Through Selective Association," which is incorporated herein by reference.

BACKGROUND OF THE INVENTION

1. Field of the Invention

This present invention relates generally to privilege association within a multiple organization context and more specifically to managing a virtual persona through selective association with an organization from a plurality of organizations.

2. Description of the Related Art

Over the last few years many enterprises have deployed business to business (B2B) e-commerce solutions. The major difference between B2B and business to consumer (B2C) solutions is that in a B2C solution a customer typically shops on behalf of himself, whereas in a B2B solution the customer probably does not represent a person who is buying for himself. Instead, the common B2B scenario is where a person buys on behalf of an organization. Increasingly this person may buy on behalf of more than one division of an organization or even more than one company. When such a buyer, who represents multiple divisions or organizations, is purchasing from a single seller there is a need to distinguish his or her privileges and attributes per buyer organization he represents. As an example, if Bob is a buyer for both ACME and EMCA organizations then the shipping addresses he is entitled to use when he buys for ACME will be different from that of EMCA. Additionally, contractual entitlements with the seller will be different with respect to the buyer organization he represents.

The typical solution to this issue, where there are multiple buyer organizations, some of which may be represented by a single person, is to have the person register a separate identity for each buyer instance they represent. This technique does solve the problem, but it has a number of drawbacks including:

The buyer typically will have to maintain multiple identities on the system with different user logon Ids and passwords.

Whenever the buyer needs to update their personal profile information they will have to remember to manually update all other identities to synchronize the identities they maintain on the system.

When a site administrator gives a buyer a certain personal privilege the administrator will have to determine all the identities the buyer has on the system and assign this privilege to each one of the buyer identities.

Having the person represented as a separate identity for each buyer organization typically represents is a drain on the system resources due to replication.

As the number of buyer organizations represented by a single buyer increases the deficiencies listed previously typically becomes increasingly unmanageable. For example using the diagram of FIG. 2, there is depicted a typical current multiple organization situation as may be found in a commerce environment. While a commerce environment is used in the example, the example is not meant to be restricted to such environments as the principles apply to similar situations and environments. The apex of multiple organization commerce system 200 is root organization 205. Associated with root organization 205 are three buyer organizations. Buyer A 225 organization has associated Buyer A users 245 and entitlement account A 250. The entitlement account provides a representation or instance of the customer/buyer. From a seller perspective, a seller does not deal with buyer organizations, but rather with accounts. The typical industry standard practice is to map an account to an organization. In this way, when a buyer user becomes associated with an organization within their session, they become entitled to shop on behalf of that organization's account, and also accounts of any child organizations. Similarly Buyer B 220 has associated Buyer B users 240 and entitlement account B 255, while Buyer C 215 organization has associated Buyer C users 235 and entitlement account C 260. For a single seller 210 having store 270, it would be necessary to create a distinct buyer identity under each of the buyer organizations in order to be able to shop on behalf of all three buyers as shown by the doffed arrow of Registered Customer role 280.

It would therefore be highly desirable to have a means for allowing a more efficient way to generally provide user support across multiple accounts.

SUMMARY OF THE INVENTION

Conveniently, software exemplary of an embodiment of the present invention allows for a solution to the problem by allowing a single person to represent multiple organizations, for example the buyer organizations of the previous example. An embodiment may typically provide support for a user to act on behalf of an account in the form of a virtual persona and also provide the ability to manage the assignment of access rights allowing only prescribed privileged users to act on behalf of an account. This may then be accomplished through registration of a single identity for the user or person on the system, while allowing that person to then select the desired buyer organization to represent for a particular purchasing session (which will be stored in the user's session). A user session is an effective persistence means for persisting state information across a series of requests from a user. The user session information may be typically stored on a server rather than on a client basis. The list of buyer organizations available for representation may then be restricted to only those in which the user plays the 'Organization Participant' role, thereby extending the previous definition of the user to that of the virtual persona. When the user chooses to represent a buyer organization in a purchasing session; attributes and privileges associated with this buyer organization are then 'inherited' by virtue of the business logic using the buyer organization to render information to be viewed or manipulated, thereby defining the persona instance. The attributes and privileges are then removed from the buyer when the buyer chooses to represent another buyer organization (and replaced by those of the other buyer organization) or ends the session.

Using this technique each user can become associated with any of the buyer organizations for which the user is privileged. By making the association dynamic, content from the point of selection forward will be tailored to the user and the buyer organization for which the user is actively shopping. The technique may also be used in other situations not related to the commerce buyer example being discussed.

In one embodiment of the instant invention there is provided a data processing system-implemented method for directing a data processing system to manage a virtual persona within a user session through selective association of the user with an organization from among a plurality of permitted organizations. The data processing system-implemented method comprising: selectively specifying the organization from a plurality of permitted organizations; inheriting attributes and privileges associated with the selectively specified organization; persisting the inherited attributes and privileges with the session; and tailoring the session content in accordance with the inherited attributes and privileges.

In another embodiment of the instant invention there is provided a data processing system for managing a virtual persona within a user session through selective association of the user with an organization from among a plurality of permitted organizations. The data processing system comprising: a selector for selectively specifying the organization from a plurality of permitted organizations; inheritance means for inheriting attributes and privileges associated with the selectively specified organization; persistence means for persisting the inherited attributes and privileges with the session; and tailoring means for tailoring the session content in accordance with the inherited attributes and privileges.

In another embodiment of the instant invention there is provided an article of manufacture for directing a data processing system to manage a virtual persona within a user session through selective association of the user with an organization from among a plurality of permitted organizations. The article of manufacture comprising: a program usable medium embodying one or more instructions executable by the data processing system, the one or more instructions comprising: data processing system executable instructions for selectively specifying the organization from a plurality of permitted organizations; inheriting attributes and privileges associated with the selectively specified organization; persisting the inherited attributes and privileges with the session; and tailoring the session content in accordance with the inherited attributes and privileges.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate embodiments of the present invention by example only.

Like reference numerals refer to corresponding components and steps throughout the drawings.

DESCRIPTION OF THE PREFERRED EMBODIMENT

Figure 1:
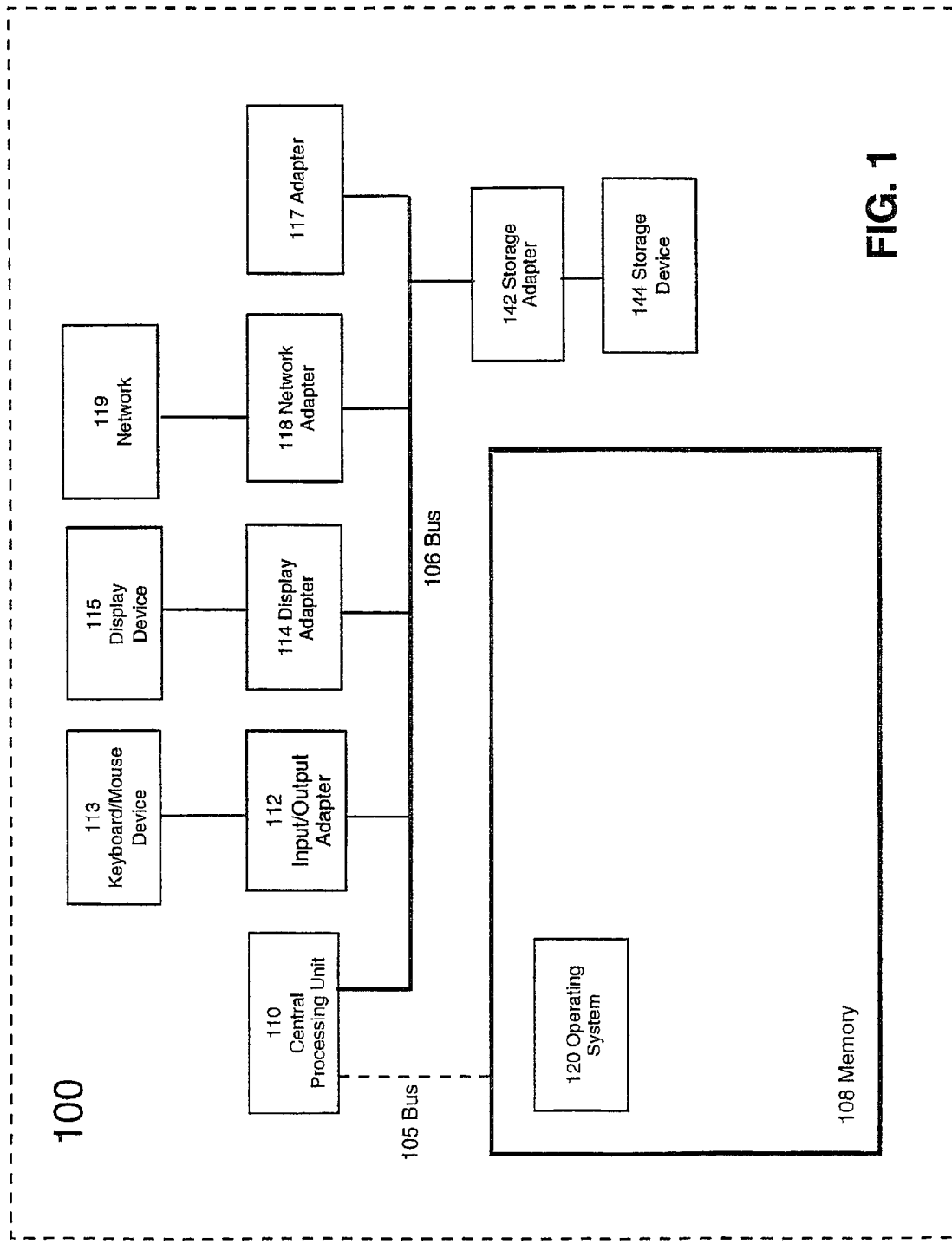
FIG. 1 is a block diagram of a typical system in which an embodiment of the present invention may be implemented.

FIG. 1 depicts, in a simplified block diagram, a computer system 100 suitable for implementing embodiments of the present invention. Computer system 100 has a central processing unit (CPU) 110, which is a programmable processor for executing programmed instructions stored in memory 108. Memory 108 can also include hard disk, tape or other storage media. While a single CPU is depicted in FIG. 1, it is understood that other forms of computer systems can be used to implement the invention, including multiple CPUs. It is also appreciated that the present invention can be implemented in a distributed computing environment having a plurality of computers communicating via a suitable network 119, such as the Internet.

CPU 110 is connected to memory 108 either through a dedicated system bus 105 and/or a general system bus 106. Memory 108 can be a random access semiconductor memory for storing components of an embodiment of the present invention as will be described later. Memory 108 is depicted conceptually as a single monolithic entity but it is well known that memory 108 can be arranged in a hierarchy of caches and other memory devices. FIG. 1 illustrates that operating system 120 also may reside in memory 108 as may other typical system utilities and services including editors and command processors.

Operating system 120 provides functions such as device interfaces, memory management, multiple task management, and the like as known in the art. CPU 110 can be suitably programmed to read, load, and execute instructions of operating system 120. Computer system 100 has the necessary subsystems and functional components to implement support for embodiments of the present invention such as data structures as will be discussed later. Other programs (not shown) include other server software applications in which network adapter 118 interacts with the other server software application to enable computer system 100 to function as a network server via network 119.

General system bus 106 supports transfer of data between various subsystems of computer system 100. While shown in simplified form as a single bus, bus 106 can be structured as multiple buses arranged in hierarchical form. Display adapter 114 supports video display device 115, which is a cathode-ray tube display or a display based upon other suitable display technology that may be used to depict results provided by an implementation of an embodiment of the present invention. The Input/output adapter 112 supports devices suited for input and output, such as keyboard or mouse device 113, and a disk drive unit (not shown). Storage adapter 142 supports one or more data storage devices 144, which could include a magnetic hard disk drive or CD-ROM drive although other types of data storage devices can be used, including removable media for storing data files such as those managed or obtained in support of an implementation of an embodiment of the present invention.

Adapter 117 is used for operationally connecting many types of peripheral computing devices to computer system 100 via bus 106, such as printers, bus adapters, and other computers using one or more protocols including Token Ring, LAN connections, as known in the art. Network adapter 118 provides a physical interface to a suitable network 119, such as the Internet. Network adapter 118 includes a modem that can be connected to a telephone line for accessing network 119. Computer system 100 can be connected to another network server via a local area network using an appropriate network protocol and the network server can in turn be connected to the Internet. FIG. 1 is intended as an exemplary representation of computer system 100 by which embodiments of the present invention can be implemented. It is understood that in other computer systems, many variations in system configuration are possible in addition to those mentioned here.

Although FIG. 1 shows functions being performed within a single system, system 100, it is likely that the actual embodiments would employ several servers and systems functioning cooperatively to manage large numbers of users. The various functions just described may be distributed among several data processing systems as dictated by processing needs while communicating as required through a network 119 such as the Internet via network adapter 118. The functions may be logically separate while on a single physical system as shown or physically separate and dispersed among a plurality of interconnected systems without impact on the basic principles and service.

Figure 2:
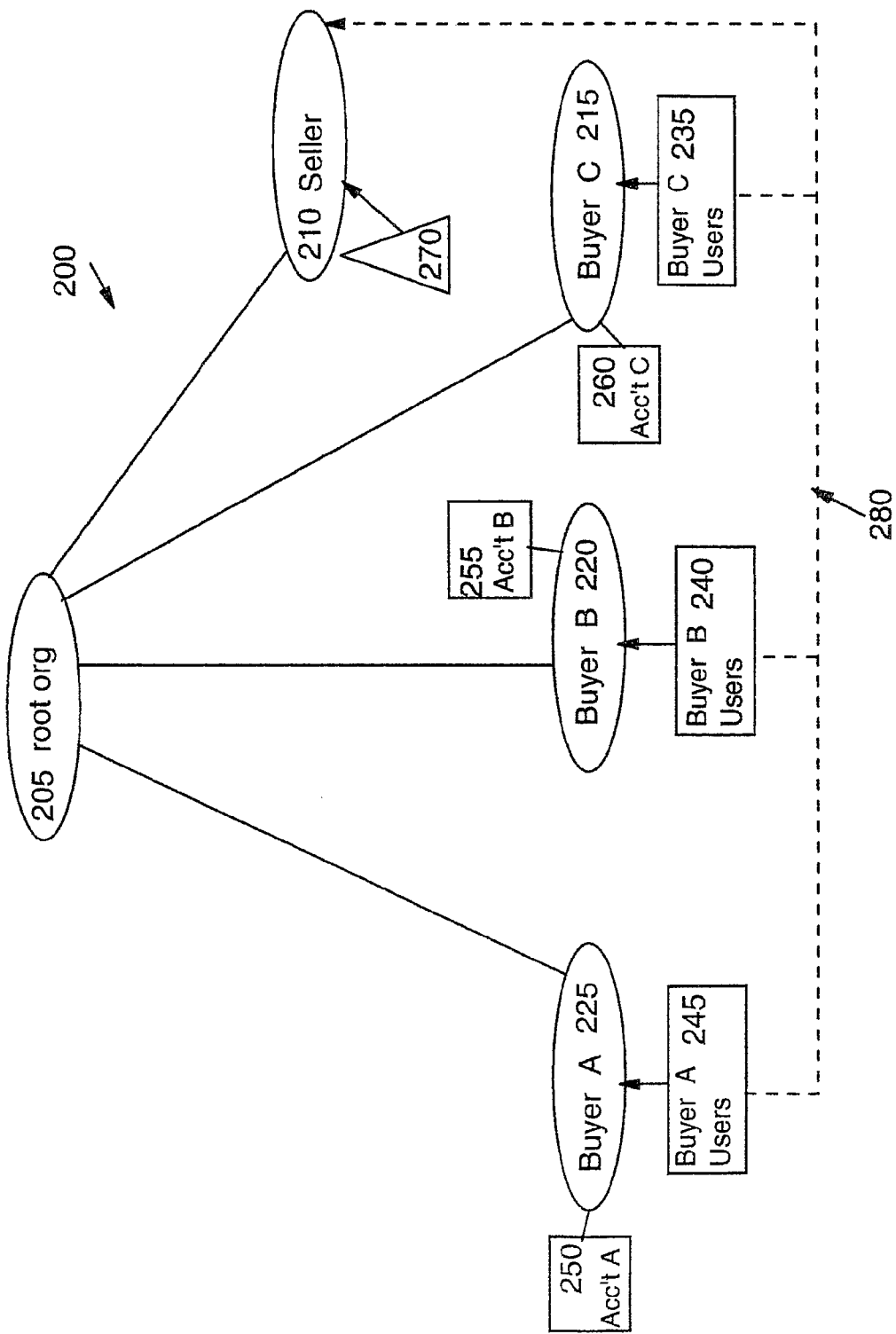
FIG. 2 is a block diagram of a current commerce situation which may operate using the system or systems of FIG. 1.
Figure 3:
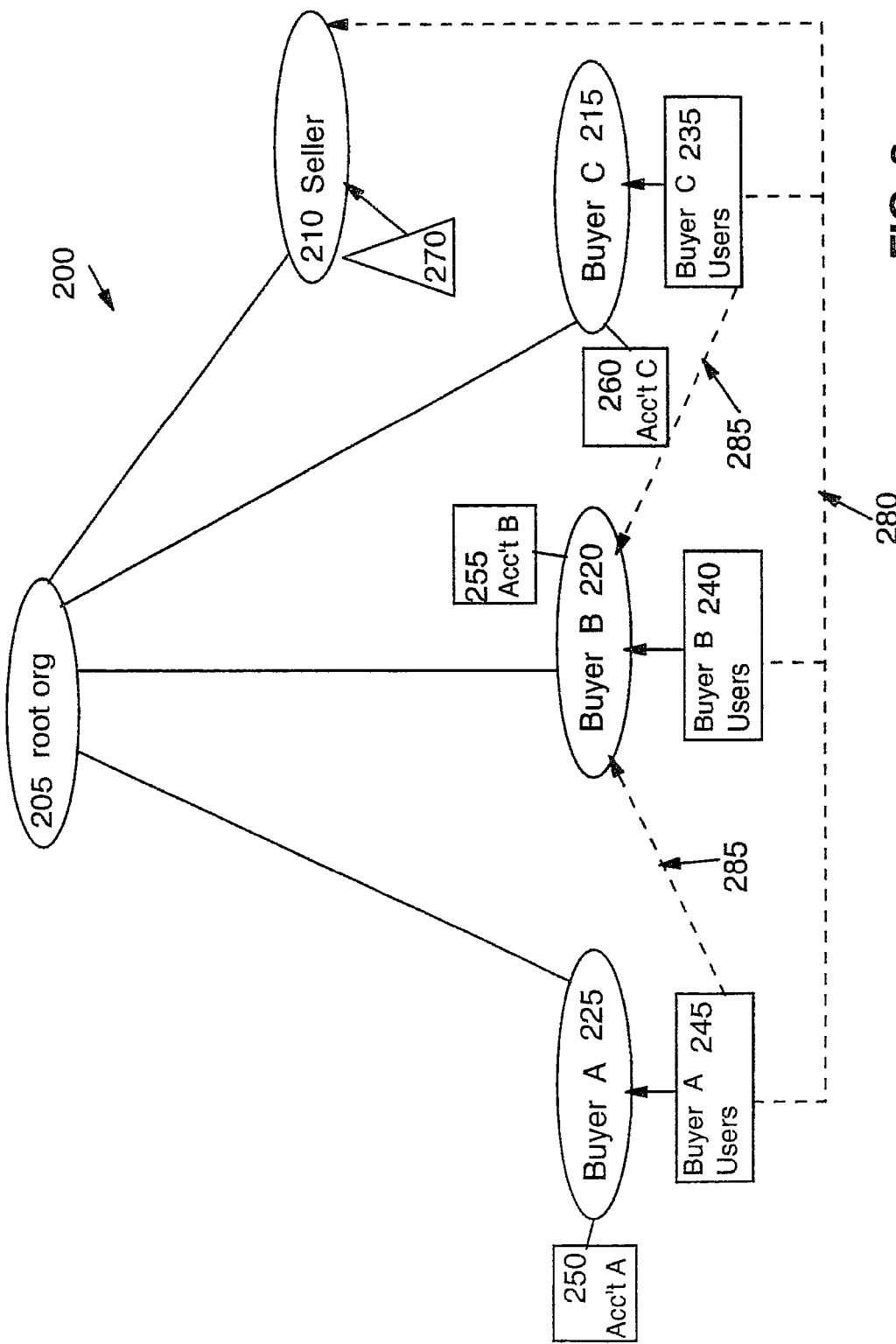
FIG. 3 is a block diagram of an embodiment of the present invention as may be supported by the system or systems of FIG. 1.

In a more particular illustration of an embodiment of the present invention, FIG. 3 is a block diagram illustrating a similar multiple organization system as in FIG. 2. It is noted that as before in FIG. 2 line 280 represents the Registered Customer role, which indicates that the user is allowed to shop in the seller's store. However Line 285 has been added (not evident in FIG. 2) representing the Organization Participant role, and indicates that Buyer A User 245 is allowed to shop on behalf of Buyer B Organization 220, and likewise that Buyer C User 235 is allowed to shop on behalf of Buyer B Organization 220. This new capability allows the user of one organization to perform actions on behalf of another organization in the form of a virtual persona through selective association with that organization.

Upon authentication to the site, the buyer is presented with a selection of buyer organizations for which he is allowed to act on behalf. The buyer is only allowed to choose one of the organizations (A, B, or C) as the buyer cannot simultaneously be a buyer for two or more organizations. Upon selection of a buyer organization, the user's session is populated appropriately to indicate the organization, for which the buyer is acting on behalf, for all subsequent requests thereby assuming the persona related to the selected organization.

The business logic that processes the requests submitted by the buyer needs to process information with respect to the buyer organization within the user's session. As an example, if the business logic is displaying possible shipping addresses to a user who has Buyer A 225 as the active organization in the session, then only the shipping addresses of that buyer organization should be displayed. Stated broadly, the business logic then allows any operation data on the site to be scoped to the currently active organization. For example, order history, requisition lists, user preferences can all be filtered based on the currently active organization.

The buyer may then switch buyer organizations at anytime, for example by going to a form to select a buyer organization from a list of available organizations for which the buyer is allowed to represent. Also, when the buyer ends the current session either by closing the browser or by logging off from the site any buyer organization association previously in effect is terminated and the data is removed from the server.

Implementation of an embodiment of the present invention typically comprises components for: use of a role to indicate the ability to act on behalf of an organization; use of the user's session to find the desired buyer organization; and a capability of setting the organization within a user's session.

The use of a role indicates a buyer ability to act on behalf of an organization. The concept of a role is therefore used to indicate the ability to act on behalf of an account, establishing an active persona. By granting a user the 'Organization Participant' role in an organization, it implies that the user can shop using any account(s) owned by that organization or any of its descendant organizations, thereby establishing the scope of the current persona.

Having all components use the session information to find the active organization provides a different approach from previous implementations. Unlike previous solutions, whereby entitlement was driven based on the user's location in an organizational hierarchy, embodiments of the present invention leverage a user's session to store the active organization. This information maintained on a server may then be leveraged to target promotions and campaigns, or to filter content for display purposes. Additionally the active organization in the session may be used for access control purposes, thereby enabling certain privileges; the user may be entitled to perform actions against resources based on the organization that is being represented.

Further support is provided for the setting of the organization within the user's session. In one embodiment of the present invention there may typically be provided an operation or transaction that can be used to switch the organization in the user's session. The change is made permanent until another organization is selected through this operation. This capability typically encompasses access control for restricting selections to enabled users, and the transaction "setting" logic itself.

For example, in a sample implementation as shown in FIG. 3 a user can shop on behalf of any organization where the user has been permitted to have the 'Organization Participant' role (one organization at a time is permitted). The organization Id for this organization becomes part of the user's session information, and is leveraged by session dependent objects including access control, contracts, promotions, and product or service order components.

It may be seen that Buyer A 245 user is granted the 'Organization Participant' role 285 in the Buyer B 220 organization. This means that Buyer A 225 can shop on behalf of accounts owned by his own organization Account A 250 or by Buyer B 220 organization and Account B 255. The persona of Buyer A has been enabled to allow selection of roles in either A or B organizations. In a similar manner Buyer C 215 can shop on behalf of accounts owned by his own organization Account C 260 or by Buyer B 220 organization and Account B 255.

An external interface may be used to provide a transaction or similar mechanism by which a user such as Buyer A User 245 becomes associated with an organization such as Buyer A 225 or Buyer B 220. Typical access control mechanisms ensure that a user can only associate with an organization if the user is entitled to do so through the organizational hierarchy providing a means for inheritance or the 'Organization Participant' role 285.

In an embodiment of the present invention, all roles are typically scoped to an organization such as that of Buyer A 225. Therefore, the concept that a user can be granted a role allowing that user to shop on behalf of an organization can typically be modelled using existing role assignment mechanisms. Administrators with authority to grant roles in a particular organization will now have the authority to grant an 'Organization Participant' role 285. Once a user has been granted this role the user is permitted to select a specific organization and its descendants other than the user's own organization to shop on their behalf. This action extends the scope of the user by defining a virtual persona to include enable use of additional permitted organizations.

In support of selecting an organization the user interface aspect of an embodiment provides a persistence feature on a web site for example whereby a user can at point in time select from those allowed organizations on whose behalf the user can shop. A selector for example in the form of a selection box may be typically provided that is populated with a list of organizations in which the user may assume 'Organization Participant' role 285, as well as organizations in the user's ancestor hierarchy.

The selection of an organization will then typically cause the user's session data to be updated. The persistence mechanism for the user's session may be realized through an implementation that will store the currently active organization scoped to the active store, such as store 270. An interface to this mechanism may be provided as in the code snippet below:

```
/**
 * Sets the active organization.
 * @param value The active organization.
 */
public void setActiveOrganization(java.lang.Long nOrganization){
    inActiveOrganization = nOrganization;
}
/**
 * Gets the active organization.
 * @return The active organization.
 */
public java.lang.Long getActiveOrganization( ){
    return inActiveOrganization;
}
```

A session API to support the getting and setting of the active organization identifier such as Buyer A 225 is typically provided. For example in a typical commerce system instance there may be multiple stores deployed. The concept of an active organization within a user's session is store specific; therefore the actual setting of the active organization comes from the store session data. When the user navigates to a different store, the active organization is dynamically set or unset within the user's session as in the following:

sessionData.setActiveOrganization(storeContainer.getActiveOrganizationId( ));

Setting the active organization identifier in the user's session from the store data may be accomplished by an organization switching interface. An example of such an interface follows:

```
/**
 * Determines whether the user is allowed to switch to the specified
 * organization.
 * @return True if the switch is allowed.
 */
protected boolean isSwitchAllowed( ) throws ECException{
// true if the organization and its ancestors are unlocked, and if the
// user is allowed to switch to the organization (either is a descendant,
// or plays the 'Organization Participant' role in this organization)
    return (!isAncestralOrgsLocked( )
        &&(isParentOrganization( ) || isReguiredRolePlayed ( ))); }
/**
 * Updates the user's session to reflect the new active organization.
 *
 * @throws ECException If there are failures with the update.
 */
protected void updateSession( ) throws ECException{
    session.setActiveOrganization(inOrganizationId);
}
```

An interface to switch the organization in the user's session may be provided using helper methods as outlined in the previous code snippet. The isSwitchAllowed( ) method in the example may be used to determine if the user is even permitted to switch to the selected organization. Logic in an embodiment of an organization switch interface typically contains conditions that must be satisfied prior to permitting a user to switch to an organization. One condition may be that the organization, and all of its ancestors, must not be locked; while another condition may be the user must either be a descendant of the organization, or must be granted 'Organization Participant' role 285 in the organization, as in the previous example. These conditions may be combined in a sequential manner.

A second helper method as provided in the example may be used to set the organization in the user's session. The basic logic of a typical embodiment may be designed to first determine whether the user is allowed to switch to the requested organization and if so to persist the switch results by updating the user's session.

Further there may be provided another type of organization switching mechanism that permits a switch back to a user's home organization—effectively unsetting the organization in the user's session. In providing this support a user such as Buyer A User 245 may then be allowed to switch back to their parent organization Buyer A 225 organization, regardless if that organization had been locked.

Further use of the context sensitive support may be evident in leveraging the organization identifier stored in the user's session, where it can be read by other sensitive components as part of their logic. Enabling adaptive processing based on the organization identifier provides a tailoring means of dynamic support functions. For example support for the organization identifier context may be used to provide:

a context sensitive contract selection mechanism in which the list of available contracts will be based upon, among other criteria, the active organization;

a context sensitive selection means in which promotions can be targeted to particular organizations wherein the runtime evaluation of these promotions can be based on the organization in the user's session;

a context sensitive order display means for displaying only those orders placed on behalf of the currently active organization, in which the user's orders would be filtered based on the currently active organization;

a context sensitive patient record selection mechanism in which the list of patient records will be based upon, among other criteria, the active organization associated with the mobile doctor;

a context sensitive address book display means for displaying the user's address book, in which the user's personal addresses as well as the addresses of the currently active organization would be displayed.

Other operations typical of an exemplary commerce application including context dependent functional support are related to orders, quotes and shopcarts are typical of support provided by these techniques. Similar respective examples in other commercial or non-commercial application should also be included.

It should be understood that the present invention can be realized in hardware, software a propagated signal or combination thereof. Any kind of computer/server system(s)—or other apparatus adapted for carrying out the methods described herein—is suited. A typical combination of hardware and software could be a general purpose computer system with a computer program that when loaded and executed carries out the respective methods described herein. Alternatively a specific use computer containing specialized hardware for carrying out one or more of the functional tasks of the invention could be utilized. The present invention can also be embedded in a computer program product or a propagated signal which comprises all the respective features enabling the implementation of the methods described herein and which when loaded in a computer system is able to carry out these methods. Computer program, propagated signal software program, program or software in the present context mean the expression in any language code or notation of a set of instructions intended to cause a system having an information processing capability to perform a particular function either directly or after either or both of the following: (a)

conversion to another language, code or notation; and/or (b) reproduction in a different material form.

Of course, the above described embodiments are intended to be illustrative only and in no way limiting. The described embodiments of carrying out the invention are susceptible to many modifications of form, arrangement of parts, details and order of operation. The invention, rather, is intended to encompass all such modification within its scope, as defined by the claims.

What is claimed is:

1. A data processing system-implemented method for directing a data processing system to manage a virtual persona within a user session through selective association of the user with a buyer from among a plurality of buyers, the data processing system-implemented method comprising:

initiating a software session between a Seller and a user, wherein the user is initially associated with a Buyer A from a plurality of buyers, and wherein the software session initially utilizes software objects provided from Buyer A to authorize the user to represent Buyer A;

selectively specifying a Buyer B, from the plurality of buyers, as being an organization for which the user is to be authorized to act as an agent, wherein selectively specifying Buyer B is initiated by and performed by the user;

determining if software objects that are associated with Buyer B are locked to prevent the user from using the software objects that are associated with Buyer B, wherein the software objects that are associated with Buyer B are selectively lockable to prevent the user from using the software objects that are associated with Buyer B, and wherein all software objects associated with Buyer A are never lockable against the user that is initially associated with Buyer A;

in response to determining that the software objects associated with Buyer B are not locked, inheriting attributes and privileges from software objects associated with Buyer B to software objects that are associated with Buyer A;

persisting the inherited attributes and privileges of software objects used in the session with the Seller, wherein the inherited attributes and privileges authorize the user to represent Buyer B instead of Buyer A in the session with the Seller, wherein the user can represent only one buyer at a time;

tailoring content of the software session in accordance with the inherited attributes and privileges such that the user is presently representing Buyer B instead of Buyer A; and in response to the user closing a browser used by the user in the session with the Seller in which the user is representing Buyer B, terminating the user's permission to act on behalf of Buyer B by deleting attributes and privileges inherited from the software objects associated with Buyer B, and returning, to the user, permission to represent Buyer A in the session with the Seller.

2. The data processing system-implemented method of claim 1, wherein the software session is controlled by a session bean in a server that directs content to the user, and wherein the session bean filters and enhances content sent from the Seller to the user while the user is representing Buyer B.

3. The data processing system-implemented method of claim 1, wherein the step of selectively specifying further comprises:

determining that the user has an "Organization Participant" role in the specified organization.

4. The data processing system-implemented method of claim 2, wherein the software session is between a patient records database and the user who represents a mobile health care professional instead of between a buyer and a seller, and wherein the mobile health care professional is permitted to access records for a selected organization, from a plurality of permitted organizations, as described by the session bean.

5. The data processing system-implemented method of claim 1, wherein the user is able to represent, to the Seller, a single one of the plurality of buyers by using another buyer from the plurality of buyers as a gateway to the seller.

6. The data processing system-implemented method of claim 1, wherein the step of tailoring further comprises at least one organization dependent function enabling session context sensitive processing using the inherited attributes and privileges to direct the dependent function processing of objects including contract entitlement, promotion determination, pricing quotations, targeted advertising, addressing and orders, quotes and shopcart processing.

7. The data processing system-implemented method of claim 1, wherein the plurality of buyers further comprises organizations for which the user has been assigned a participant privilege role, thereby enabling the user to act on behalf of one or more of the buyers.

8. A data processing system for managing a virtual persona within a user session through selective association of the user with a buyer from among a plurality of buyers, the data processing system comprising a processor and a computer readable medium having:

an initiator for initiating a software session between a Seller and a user, wherein the user is initially associated with a Buyer A from a plurality of buyers, and wherein the software session initially utilizes software objects provided from Buyer A to authorize the user to represent Buyer A;

a selector for selectively specifying a Buyer B from the plurality of buyers, as being an organization for which the user is authorized to act as an agent, wherein selectively specifying Buyer B is initiated by and performed by the user;

determining logic for determining if software objects that are associated with Buyer B are locked to prevent the user from using the software objects that are associated with Buyer B, wherein the software objects that are associated with Buyer B are selectively lockable to prevent the user from using the software objects that are associated with Buyer B, and wherein all software objects associated with Buyer A are never lockable against the user that is initially associated with Buyer A;

inheritance logic for, responsive to a determination that the software objects associated with Buyer B are not locked, inheriting attributes and privileges from software objects associated with Buyer B to software objects associated with Buyer A;

persistence logic for persisting the inherited attributes and privileges of software objects used in the session with the Seller, wherein the inherited attributes and privileges authorize the user to represent Buyer B instead of Buyer A in the session with the Seller, wherein the user can represent only one buyer at a time;

tailoring logic for tailoring content of the session in accordance with the inherited attributes and privileges such that the user is presently representing Buyer B instead of Buyer A; and terminating logic for, in response to the user closing a browser used by the user in the session with the Seller in which the user is representing Buyer B, terminating the user's permission to act on behalf of Buyer B by deleting attributes and privileges inherited from the software objects associated with Buyer B, and returning, to the user, authority to represent Buyer A in the session with the Seller.

9. The data processing system of claim 8, wherein the software session is controlled by a session bean in a server that directs content to the user, and wherein the session bean filters and enhances content sent from the Seller to the user while the user is representing Buyer B.

10. The data processing system of claim 8, wherein the selector for selectively specifying further comprises determination logic for:
    determining that the user has an "Organization Participant" role in the specified organization.

11. The data processing system of claim 9, wherein the Java session wherein the software session is between a patient records database and the user who represents a mobile health care professional instead of between a buyer and a seller, and wherein the mobile health care professional is permitted to access records for a selected organization, from a plurality of permitted organizations, as described by the session bean.

12. The data processing system of claim 8, wherein the selector for selectively specifying further comprises specification of a parent organization, wherein organization switching occurs regardless of organization lock status.

13. The data processing system of claim 8, wherein the tailoring means further comprises at least one organization dependent function enabling session context sensitive processing using the inherited attributes and privileges to direct the dependent function processing of objects including contract entitlement, promotion determination, pricing quotations, targeted advertising, addressing and orders, quotes and shopcart processing.

14. The data processing system of claim 8, wherein the selector for selectively specifying further comprises scoping information for a currently active organization to an active store.

15. The data processing system of claim 9, wherein the plurality of buyers further comprises organizations for which the user has been assigned a participant privilege role, thereby enabling the user to act on behalf of one or more of the buyers.

16. A computer readable tangible medium embodied with a computer program product for directing a data processing system to manage a virtual persona within a user session through selective association of the user with an organization from among a plurality of permitted organizations, the computer program product embodying instructions executable by the data processing system, said instructions comprising:
    data processing system executable instructions for initiating a software session between a Seller and a user, wherein the user is initially associated with a Buyer A from a plurality of buyers, and wherein the software session initially utilizes software objects provided from Buyer A to authorize the user to represent Buyer A;
    data processing system executable instructions for selectively specifying a Buyer B, from the plurality of buyers, as being an organization for which the user is authorized to act as an agent, wherein selectively specifying Buyer B is initiated by and performed by the user;
    data processing system executable instructions for determining if software objects that are associated with Buyer B are locked to prevent the user from using the software objects that are associated with Buyer B, wherein the software objects that are associated with Buyer B are selectively lockable to prevent the user from using the software objects that are associated with Buyer B, and wherein all software objects associated with Buyer A are never lockable against the user that is initially associated with Buyer A;
    data processing system executable instructions for in response to determining that the software objects associated with Buyer B are not locked, inheriting attributes and privileges from software objects associated with Buyer B to software objects that are associated with Buyer A;
    data processing system executable instructions for persisting the inherited attributes and privileges of software objects used in the session with the Seller, wherein the inherited attributes and privileges authorize the user to represent Buyer B instead of Buyer A in the session with the Seller, wherein the user can represent only one buyer at a time;
    data processing system executable instructions for tailoring content of the software session in accordance with the inherited attributes and privileges such that the user is presently representing Buyer B instead of Buyer A; and
    data processing system executable instructions for, in response to the user closing a browser used by the user in the session with the Seller in which the user is representing Buyer B, terminating the user's permission to act on behalf of Buyer B by deleting attributes and privileges inherited from the software objects associated with Buyer B, and returning, to the user, authority to represent Buyer A in the session with the Seller.

17. The computer readable tangible medium of claim 16, wherein the data processing system executable instructions for selectively specifying further comprises data processing system executable instructions for specification of an alternate permitted organization other than a user parent organization.

18. The computer readable tangible medium of claim 16, wherein the data processing system executable instructions for selectively specifying further comprises data processing system executable instructions for: determining that the user has an "Organization Participant" role in the specified organization.

19. The computer readable tangible medium of claim 16, wherein the data processing system executable instructions for inheriting further comprises data processing system executable instructions for acquiring access control determined privileges for a specified organization.

20. The computer readable tangible medium of claim 16, wherein the inherited attributes and privileges persistently authorize the user to represent the Buyer B until another organization is selected by the user.

* * * * *